US008589137B2

(12) United States Patent
Wenzel et al.

(10) Patent No.: US 8,589,137 B2
(45) Date of Patent: Nov. 19, 2013

(54) METHOD AND SYSTEM FOR DETERMINING THE SOLVENT ACCESSIBLE SURFACE AREA AND ITS DERIVATIVES OF A MOLECULE

(75) Inventors: Wolfgang Wenzel, Weingarten (DE); Horacio Emil Perez-Sanchez, Murcia (ES); Konstantin Klenin, Stutensee (DE)

(73) Assignee: Karlsruher Institut fuer Technologie, Karlsruhe (DE)

( * ) Notice: Subject to any disclaimer, the term of this patent is extended or adjusted under 35 U.S.C. 154(b) by 0 days.

(21) Appl. No.: 13/039,874

(22) Filed: Mar. 3, 2011

(65) Prior Publication Data
US 2011/0218788 A1 Sep. 8, 2011

(30) Foreign Application Priority Data

Mar. 4, 2010 (EP) .................................. 10002203

(51) Int. Cl.
*G06G 7/58* (2006.01)
(52) U.S. Cl.
USPC ............................................. 703/11; 703/12
(58) Field of Classification Search
None
See application file for complete search history.

(56) References Cited

U.S. PATENT DOCUMENTS

2006/0121455 A1 6/2006 Goddard

OTHER PUBLICATIONS

Dynerman et al. Journal of Computational Biology, vol. 16, No. 4, 2009, 523-527.*
Dynerman et al. IEEE/ACM Supercomputing 2008, pp. 1-28.*
Juba et al. J. Mol. Graph. Model., vol. 27, No. 1, pp. 82-87.*
Fraczkiewicz R. et al. J. Comp. Chem., 1998, vol. 19, No. 3, pp. 319-333.*
Sridharan S. et al. (1995) , J. Comp. Chem., vol. 16, No. 8, pp. 1038-1044.*
Perrot G. et al. (1992) J. Comp. Chem., vol. 13, No. 1, pp. 1-11.*
European Search Report of EP 10 00 2203 Dated Aug. 17, 2010.

\* cited by examiner

*Primary Examiner* — Michael Borin
(74) *Attorney, Agent, or Firm* — Venable LLP; Robert Kinberg; Christopher B. Tokarczyk

(57) ABSTRACT

A method for performing a molecular dynamics simulation for determining the solvent accessible surface area of a molecule with respect to atomic coordinates, the molecule comprising a plurality of atoms, a sphere being assigned to each atom, and each sphere comprising a radius and a center position.

9 Claims, 2 Drawing Sheets

METHOD AND SYSTEM FOR DETERMINING THE SOLVENT ACCESSIBLE SURFACE AREA AND ITS DERIVATIVES OF A MOLECULE

CROSS-REFERENCE TO RELATED APPLICATIONS

Priority is claimed to European Patent Application No. 10002203.7 filed Mar. 4, 2010, the disclosure of which is incorporated herein by reference in its entirety.

BACKGROUND OF THE INVENTION

The invention relates to a method for determining the solvent accessible surface area of a molecule with respect to atomic coordinates, wherein the molecule comprises a plurality of atoms, each atom is represented by a sphere having a radius and a center position, and the solvent accessible surface area of the molecule is determined depending on the sum of the solvent accessible surface areas of its atoms.

The method also relates to a system for determining the derivatives of the solvent accessible surface area of a molecule with respect to atomic coordinates, wherein the molecule comprises a plurality of atoms, each atom is represented by a sphere having a radius and a center position, and the system comprises means for determining the derivatives of the solvent accessible surface area of atoms depending on the radius and center position of the spheres.

The invention further relates to a processor in a system for performing a molecular dynamics simulation for a system of molecules comprised of atoms and to a computer program for the molecular dynamic simulations based on determining the solvent accessible surface area of atoms and its derivatives, wherein the computer program is executable on a processor in a system for performing a molecular dynamics simulation.

In order to determine the positions, velocities, and energies of the particles, e.g. the atoms, in the simulations over a period of time, knowledge about the forces between the particles is required. For determining the energy and other thermodynamic properties of the system, the solvent accessible surface of each atom is required. For determining the forces acting on each atom, derivatives of the solvent accessible surface of each atom are required. Techniques known as molecular dynamics determine the positions, velocities and properties of the particles by simulating the physical process in a computer model and thus give insight into all properties of the system and the interaction of the molecules with high temporal and spatial resolution. Molecular dynamics is frequently used in the study of proteins and other biomolecules, as well as in materials science. Molecular dynamics is a technique to perform virtual experiments that increasingly replaces the need to perform costly experiments in the laboratory. Molecular dynamics simulations also permit the study of processes not readily observable with present day experimental techniques (because of the small size of the system, the speed of the process or both).

One kind of molecules are proteins, which perform the vast majority of all biological processes in all cells of plants, animals or humans. The function of these biological macromolecules is regulated in a biological system by binding small molecules (ligands) to the proteins or by the interaction of proteins with other proteins or by the interaction of proteins with DNA. When the function of a certain protein is involved in a certain disease, it is possible to interfere with its function using artificial ligands, which are the most common mechanism of drugs in use today. Since the structure of many (>40.000) disease-relevant proteins is known, in-silico design of new drugs is possible by performing molecular dynamics simulations that simulate the process of binding of the small molecule to the protein in question. In order to influence the function of a protein, a drug has to bind better to the protein than the natural ligand. Currently, molecular dynamics is the most accurate method to determine the binding-strength of both the natural ligand and the proposed molecules.

Furthermore, if a drug has known side effects, it is possible to link the drug molecules with the target molecules so that the drug works mostly in the affected cells, for instance, in a cell affected by cancer. Molecular dynamics can be used to determine how such drug-target complexes bind to the target protein of the drug and how the drugs enter the cell through the membrane.

Molecular dynamics are also used in order to determine the function of a protein, aspects of its structure, the interaction between proteins, and the interaction of proteins and other molecules, such as DNA or man-made molecules emerging from research in the nano sciences.

In the field of materials sciences, molecular dynamics are used to determine material properties, for example the structure and function of organic light emitting diodes, the efficiency of lithium-ion batteries, or the structure and function of nano materials, e.g. single atom transistor or carbon nanotube sorting.

Summarized, molecular dynamics is a method to replace experiments in the laboratory in many fields of science and to permit analysis of the time-dependent behaviour of a molecular system. This knowledge is used to investigate the structure, dynamics, and thermodynamics of biological molecules, their complexes and systems relevant for materials research.

In order to obtain accurate results in molecular dynamics simulations the system must be modelled in its experimentally relevant environment, which is particularly important for systems in solution. One possibility to perform such simulations is to include a large number of solvent molecules explicitly in the simulation, which is performed in a finite simulation volume. In order to avoid edge effects at surface of this volume, periodic boundary conditions are required in such simulations. In a simulation with periodic boundary conditions the system is mathematically replicated periodically in each space direction, such that the particle leaving the simulation volume at the left automatically re-enters it from the right. Periodic boundary conditions permit simulation of an infinite systems, which has no boundaries and therefore no edge effects.

An alternative to this approach are implicit solvent models, which compute forces and properties of the molecular system excluding the solvent by introducing effective energy contributions/forces acting on the atoms of the system. The use of implicit solvent models significantly reduces the number of atoms that have to be simulated and thereby the number of instructions a processor must perform to simulate the system. Use of implicit solvent models also avoids the use of periodic boundary conditions, which simplifies significantly the computation of particular energy contributions, such as electrostatic interactions, which occur in almost all molecular systems.

Performing molecular dynamics simulations has limitations in size and time scale due to the available computing resources. Therefore, molecular dynamics simulations of the required complexity cannot be executed on standard processors, because the processing power of such standard processors is too low. This led to the development of special processors and/or architectures in order to substitute or support standard (main-)processors while performing molecular dynamics simulations. Such special processors and/or architectures include the Cell processor (IBM/SONY), graphics processing units (GPUs) (ATI/NVIDIA), and FPGA (Field Programmable Gate Array) processors, which can be integrated into standard PC-type computers.

Currently, state-of-the-art GPUs can perform over 500 billion arithmetic operations per second. According to recent advances in GPU hardware and software architecture, such processing units can now be utilized for general purpose computing and in particular for molecular dynamics simulations. Although these special processors and architectures are—at least theoretically—up to 1000 times faster than standard processors known from personal computers, this hypothetical gain cannot be realized in simulating molecular dynamics using periodic boundary conditions, because of technical reasons, e.g. the high number of inter-processor communications and the high number of processor-memory communications that are needed to evaluate certain mathematical expressions when using periodic boundary conditions.

Such simulations can be performed much faster using special processors when using implicit solvent models. Most implicit solvent models require the computation of the solvent accessible surface and its derivatives for each atom of the molecule at each time-step of the simulation. Typical simulations performed today comprise 100-100.000.000 atoms for which forces must be computed in $10^6$-$10^{12}$ simulation steps, resulting in the need to compute up to $10^{20}$ derivatives of the solvent accessible surface area in one simulation. The determination of the derivatives of the solvent accessible surface area significantly contributes to the total computing complexity of the molecular dynamics simulation, because to date an exact expression for the computation of the derivatives of the solvent accessible surface area is not available. Using established approximate methods for the computation of the derivatives of the solvent accessible surface area requires 10.000-100.000 computer operations for each atom and time-step (depending on the accuracy of the approximation). Using approximate methods to compute the derivatives of the solvent accessible surface thus induces a high cost of computation and reduces its accuracy, because the use of approximate methods results in errors in the computation of the forces and the computed properties of the system It is therefore an object of the present invention to provide an exact method and system for determining the derivatives of the solvent accessible surface area of a molecule that can be used e.g. in molecular dynamics simulations and enable to perform these simulations significantly faster and more accurate than currently known methods.

SUMMARY OF THE INVENTION

The present invention is based on the fact, that each molecule in a solvent comprises a plurality of atoms. Each atom of a molecule possibly contributes to the solvent accessible surface area of the molecule. The solvent accessible surface area of the molecule is determined as the sum of the solvent accessible surface areas of its atoms. The solvent accessible surface of an atom is defined as the fraction of an area of a sphere centered at the position of the atom which is not covered by spheres centered at the positions of the other atoms of the system. To compute the solvent accessible surface each atom is assigned a radius. The solvent accessible surface area of an atom, called center atom, is thus influenced by all other atoms, called neighbouring atoms, where the sum of the radii of center and neighbouring atoms is smaller than their distance. Thus, when determining the solvent accessible surface area of an atom and its derivatives, the part of the surface that is covered by other atoms has to be computed.

Within the terminology of the present invention, each atom is considered as being a sphere having a radius and a center position, wherein the center position of the sphere corresponds to the center position of the atom. This sphere is assigned to the atom. For determining the derivatives of the solvent accessible surface area of the molecule with respect to the coordinates of the atoms, the derivatives of the solvent accessible surface area of each atom, i.e. each sphere, are determined. Therefore, for each sphere the intersecting sphere(s)—if any—is(are) determined, wherein each intersecting sphere has an intersection with the surface of the currently considered sphere, defined by the intersection line. The intersecting line thus defines an intersection area on the surface of the currently considered sphere that is not accessible to the solvent, since this area is covered by the intersecting sphere.

If a sphere has more than one intersecting sphere, the intersection areas on the surface of this sphere induced by each intersecting sphere might overlap. This has to be taken into account when determining the solvent accessible surface area of an atom. Therefore, for each sphere the closed areas on its surface that are covered by one or more intersecting spheres are determined. The boundaries of these closed areas are denoted as "contours". Each contour is defined by the intersection line of at least one intersecting sphere. If the intersection areas of two or more intersection spheres overlap on the surface of the considered sphere, then the contour is defined a set of sections the intersection lines of these intersecting spheres. Each section of the intersection line that is generated by one neighbouring sphere, but not covered by an intersection with any other neighbouring sphere, is denoted as "arc".

According to the present invention, for each sphere that has at least one intersecting sphere, at least one contour is determined, wherein the contour is the boundary of the area on the surface of said sphere that is formed (a) by the intersection line of the surface of said sphere with the surface of the intersecting sphere or (b) at least by sections of at least two intersecting spheres that have an overlapping area on the surface of said sphere.

The solvent accessible surface area of this sphere is then determined as the surface of said sphere subtracted by the area contained inside contours defined by neighbouring spheres on its surface.

The present invention enables to determine exact results for the solvent accessible surface area of a molecule and its derivatives, whereas known methods only achieve approximate results. Moreover, the inventive method requires less intermediate data and can be implemented using only a small number of instructions. From this follows that the inventive method requires less memory space than known methods. Thus, if the inventive method is implemented and executed on a special processor or architecture that usually has only a small memory capacity and a small communication bandwidth for technical reasons, an improved performance of the special processor and/or architecture can be achieved. This is due to the fact that when executing the inventive method on a special processor, many thousand steps computations of the solvent accessible surface and its derivatives can be executed on the special processor without the need of communicating with peripheral devices, e.g. peripheral memories, or a main processor, since the instructions and the required data can be stored in the memory of the special processor and since the memory space needed for storing intermediate results is reduced.

According to an embodiment of the present invention, derivatives $$\frac{dS}{dr_i}$$

of the solvent accessible surface area of the atoms with respect to the position of the atoms (or spheres) are determined and the derivatives are required to determine the forces during the process of molecular dynamics simulation.

The derivative $$\frac{dS}{dr_i}$$

of the solvent accessible surface area of an atom (i.e. its sphere) with respect to the position of the intersecting atoms (i.e. the intersecting spheres) is determined by the formula $$\frac{dS}{dr_i} = \frac{\varphi_i \rho}{2}\left(1 + \frac{\rho^2 - \rho_i^2}{b_i^2}\right)e_i - \frac{\rho}{b_i}[(v_{i+1} - v_i) \times e_i],$$

wherein

S is the solvent accessible surface area of sphere B centered at the point r;

$r_i$ is the center of sphere $B_i$, wherein sphere $B_i$ is the i-th intersecting sphere of sphere B;

ρ is the radius of sphere B;

$\rho_i$ the radius of the intersecting sphere $B_i$;

$b_i=|r-r_i|$ is the distance between center r of sphere B and center $r_i$ of sphere $B_i$.

$e_i=(r_i-r)/b_i$ is the unit vector from center r of sphere B to the center $r_i$ of sphere $B_i$; and $v_i$ is the endpoint of an arc $a_i$, wherein arc $a_i$ is the part of the intersection line $I_i$ contributes to the contour $C_m$.

If the formula given above is implemented on a processor, the derivative of the solvent accessible surface can be determined exactly. In addition, using the known method requires fewer and less memory instructions than formerly known methods. Thus, thousands of such computations can be performed on a special processor without the need for communicating with the main processor or with peripheral memories.

This invention can be realized in the form of a computer program that can be run on one or more processors, in particular on a special processor and/or a special architecture, wherein the computer program is programmed to carry out the inventive method. Parts of the computer program may be run on different processors in order to carry out the inventive method. The invention is, thereby, realized by the computer program, wherein this computer program represents the invention in the same sense as the method for the execution of which the computer program is suitable. The computer program is preferably stored in a storage element, e.g. any optical or magnetic storage device. A storage element may, in particular, be a random-access-memory, a read-only-memory, a hard disk, or any portable memory device. When implemented in a computer program, the invention thus enables special processing units to perform molecular dynamics simulations more accurate and much faster than existing methods.

Further aspects of the invention are shown in the figures and described in the accompanying description.

DETAILED DESCRIPTION OF EMBODIMENTS OF THE INVENTION

In implicit solvent models used in molecular dynamics simulations a molecule is represented as a set of atoms which are modelled as partially overlapping spheres. The total solvent accessible surface of the molecule and its derivative are computed as the sum of the solvent accessible surface/derivatives of the individual atoms. Therefore, in the following description the determination of the solvent accessible surface is shown for one atom, which than has to be repeated for the other atoms. The determination of the solvent accessible surface area of several atoms can be performed in parallel.

Figure 1:
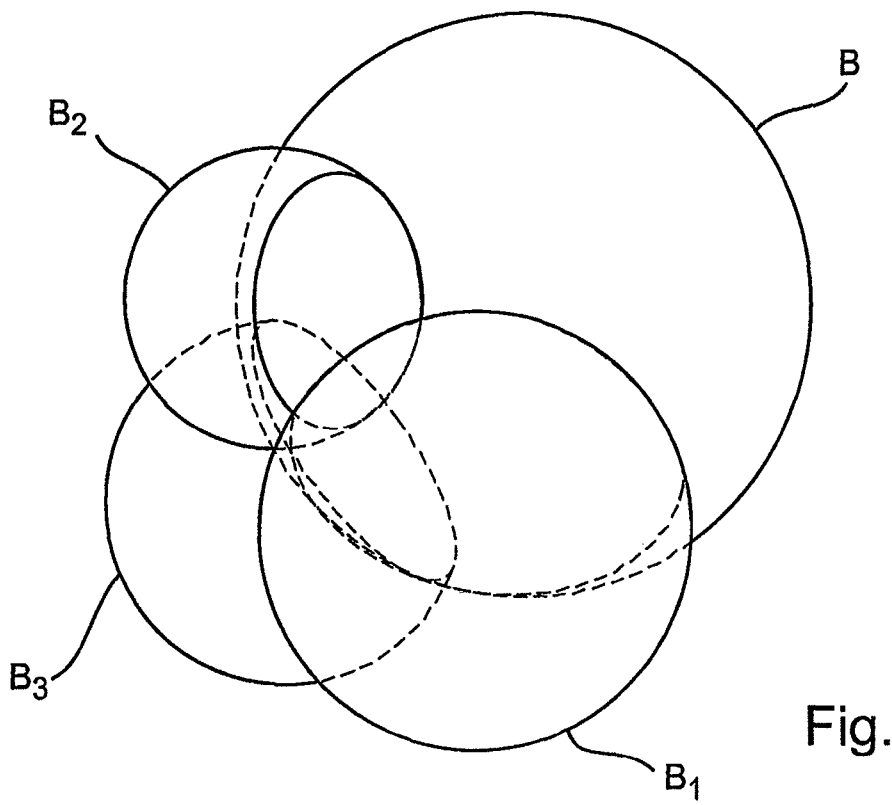
FIG. 1 is a graphic presentation of a first sphere representing a first atom and three neighbouring spheres representing three neighbouring atoms.
Figure 2:
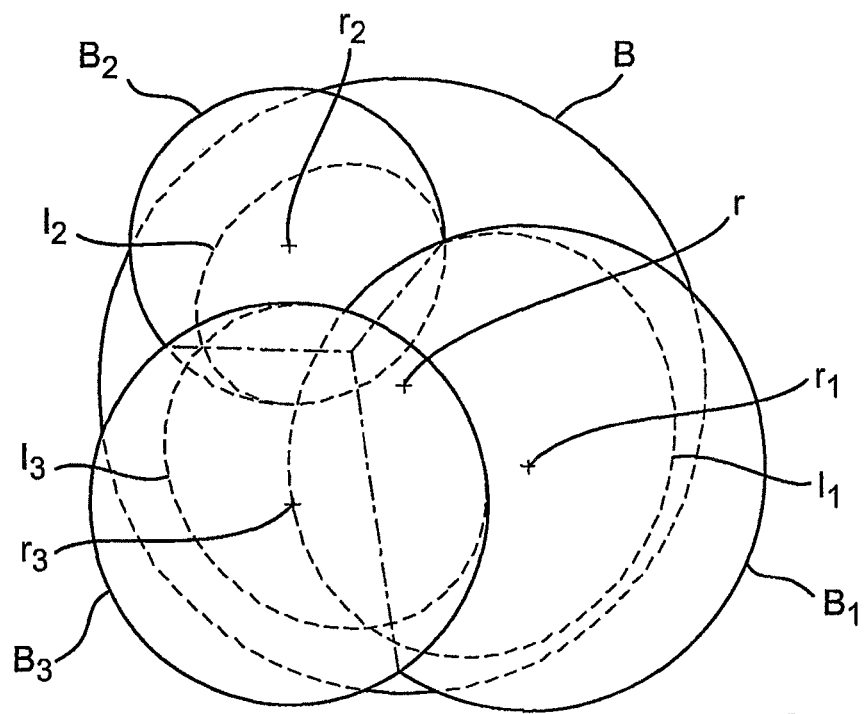
FIG. 2 shows another view of the spheres shown in FIG. 1 with labels indicating their radii.
Figure 3:
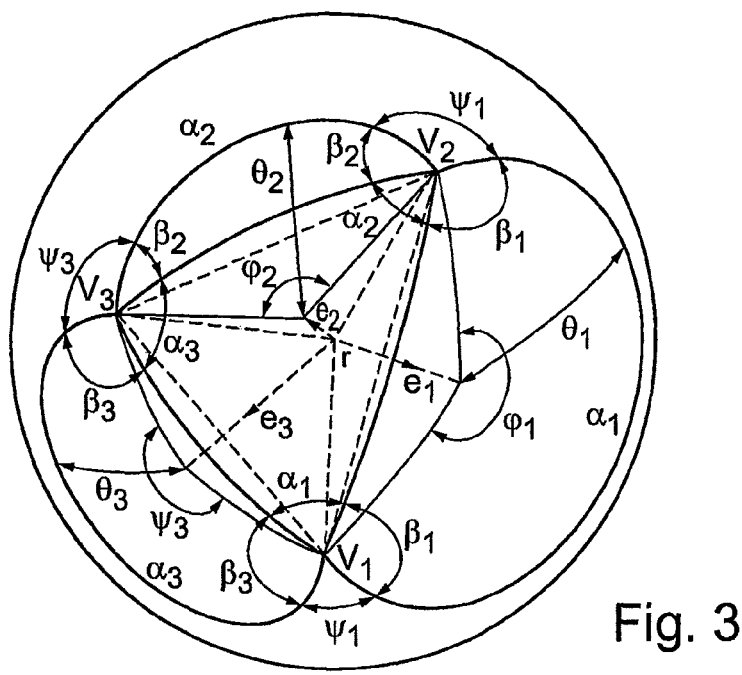
FIG. 3 shows a more detailed view of the spheres shown in FIGS. 1 and 2, including a graphic representation of several values that are used for determining the total area of the intersecting circles shown in FIGS. 1 and 2.

FIG. 1 shows as an example a central atom for which the solvent accessible surface and the derivative are to be determined. FIGS. 2 and 3 show several values required for determining the solvent accessible surface for the central atom according to an embodiment of the present invention. The following description refers to the exemplary arrangement of atoms as shown in FIGS. 1 to 3.

Each atom of the exemplary arrangement is represented by its sphere B (for the central atom), $B_1$, $B_2$, and $B_3$ (for the relevant neighbouring spheres) with radii ρ, $\rho_1$, $\rho_2$, and $\rho_3$, respectively. The positions of the center of spheres B, $B_1$, $B_2$, $B_3$ are denoted by r, $r_1$, $r_2$, and $r_3$, respectively. In this example sphere B is intersected by neighbouring spheres $B_1$, $B_2$, and $B_3$. Depending on the position of the neighbouring atoms they may intersect with the sphere of the central atom. Each intersection area on the surface of sphere B is bordered by an intersection line $I_1$, $I_2$, and $I_3$, shown as dashed circles in FIG. 2. To determine the solvent accessible surface of sphere B one must compute the area of each circle $I_1$, $I_2$, and $I_3$ on the sphere B and then subtract the mutually overlapping areas of these circles.

In order to determine the solvent accessible area, arcs $a_1$, $a_2$, $a_3$ of the intersecting circles $I_1$, $I_2$, and $I_3$ have to be determined, wherein arcs a1-a3 define the outer boundary of the connected region formed by the three circles $I_1$, $I_2$, and $I_3$.

This determination is a complex operation, because the number and arrangement of the overlapping areas depend on the position, radii and number of the neighbouring spheres.

The solvent accessible surface area of the atom B can be visualized as being the area on its surface that is not covered by the spheres of its neighbours.

Generally speaking, each set of overlapping intersection areas define a contour $C_m$ on the surface of a sphere B. Each contour $C_m$ defines an area on sphere B that can not be accessed by the solvent. Thus, when determining the solvent accessible surface area of an atom, the areas defined by each contour $C_m$ on its sphere B has to be subtracted from the surface of sphere B.

In the example shown in FIGS. 1 and 3 to 5, the intersection areas on the surface of sphere B with the intersecting spheres $B_1$, $B_2$, $B_3$ overlap with each other. Thus, these intersection areas shape a connected area on the surface of sphere B, which is shown in FIG. 3 as the hatched area denoted as contour $C_1$. The remaining areas on the surface of sphere B that are not comprised by any contour $C_1$, $C_m$ form the solvent accessible surface area S of sphere B (shown as hatched area in FIG. 4.)

Generally, each contour $C_m$ on the surface of sphere B is a boundary line that consists of one or more arcs $a_i$ resulting from the intersection with the intersecting spheres $B_i$ surrounding the neighbouring atoms. As can be seen from a combination of FIGS. 1 and 3, each arc $a_1$, $a_2$, $a_3$ is a section of an intersection line $I_1$, $I_2$, and $I_3$.

Each contour $C_m$ is therefore formed by n arcs, with n being any natural number greater than zero. By convention, the indices of arcs $a_i$ increase as one moves round counter-clockwise the contour $C_m$.

In order to determine the solvent accessible surface of the atom associated with sphere B, the area within each contour $C_m$ is determined and subtracted from the total surface area of sphere B. The following description shows how to determine the area contained within one contour, a procedure which can be repeated for each contour on the sphere.

FIG. 5 shows another view of sphere B and its intersecting spheres $B_1$, $B_2$, and $B_3$. Throughout the following description, only a single contour $C_1$ formed by arcs $a_1$, $a_2$, $a_3$ is considered. However, each atom (i.e. each sphere $B_i$) may contribute to several contours $C_1$, $C_m$, and each contour $C_1$, $C_m$ may be formed by several intersecting spheres $B_i$.

If the solvent accessible surface area is determined for simulating molecular dynamics, the forces acting on atoms have to be determined very often during the simulation process. In order to reduce the computing time, the forces are determined based on the derivatives $$\frac{dS}{dr_i}$$

of the solvent accessible surface area S with respect to the position of the neighbouring atoms (i.e. the position $r_i$ of the center of intersecting spheres $B_i$).

According to the invention, the derivative $$\frac{dS}{dr_i}$$

is determined based on the following formula:

$$\frac{dS}{dr_i} = \frac{\varphi_i \rho}{2}\left(1 + \frac{\rho^2 - \rho_i^2}{b_i^2}\right)e_i - \frac{\rho}{b_i}[(v_{i+1} - v_i) \times e_i].$$

wherein $e_i$ is the unit vector in the direction to the i-th neighbour atom (i.e. in the direction from point r to point $r_i$)

This formula can be verified based on first considering the component of gradient $$\frac{dS}{dr_i}$$

that is parallel to vector $e_i$. The total area $S_i^{(cap)}$ of the cap covered by the i-th atom (i.e. intersecting sphere $B_i$) is $$S_i^{(cap)} = 2\pi(1 - \cos\theta_i)\cdot\rho^2, \tag{1}$$

where $\theta_i$ is the angular radius of the cap as shown in FIG. 5. $\theta_i$ can be obtained by the term $$\cos\theta_i = \frac{1}{2\rho}\left(b_i + \frac{\rho^2 - \rho_i^2}{b_i}\right), \tag{2}$$

where $b_i$ is the distance between center points r and $r_i$.

By an infinitesimal increment of $b_i$, the fraction of the cap boundary contributing to the change of the covered area is equal to $$\frac{\varphi_i}{2\pi},$$

where $\varphi_i$ is the central angle of arc $a_i$. From this follows, that $$\frac{dS}{dr_i}e_i = -\frac{\varphi_i}{2\pi}\frac{dS_i^{(cap)}}{db_i} = \frac{\varphi_i\rho}{2}\left(1 + \frac{\rho^2 - \rho_i^2}{b_i^2}\right), \tag{3}$$

An infinitesimal displacement $dr_i$ of sphere $B_i$ in the direction perpendicular to $e_i$ can be treated as a rotation by an angle $\gamma_i$ (not shown in the figures) about the central point r, such that $$d\gamma_i = (e_i \times dr_i)/b_i \tag{4}$$

If the surface tension of the selected atom is $\sigma$, then $$T_i d\gamma_i = -\sigma dS \tag{5}$$

where $T_i$ is the corresponding torque. From the formulas above follows that $$dr_i(T_i \times e_i) = -\sigma b_i dS. \tag{6}$$

The inventors have realized that the torque $T_i$ acting on any line on the sphere surface depends only on the end points of the line but not on its particular shape. Thus, $T_i$ can be described as the torque acting on a geodesic that connects the end points $v_i$ and $v_{i+1}$ of arc $a_i$. For symmetry reasons, $T_i$ should be proportional to the vector $v_{i+1} - v_i$ (if i=n, the index (i+1) should be substituted by 1).

When the geodesic is rotated about an axis parallel to this vector by the full angle $2\pi$, the swept area is $4\pi\rho^2|v_{i+1}-v_i|/2\rho$. When the angle of rotation is $d\gamma_i$, the swept area changes by the factor of $d\gamma_i/2\pi$. From this follows that:

$$T_i = -\sigma dS/d\gamma_i = \sigma\rho(v_{i+1} - v_i). \tag{7}$$

From the last two formulas above follows, that $$dS = -(\rho/b_i)[(v_{i+1} - v_i) \times e_i]dr_i, dr_i \perp e_i \tag{8}$$

From a combination of formula (8) and formula (3) follows, that $$\frac{dS}{dr_i} = \frac{\varphi_i \rho}{2}\left(1 + \frac{\rho^2 - \rho_i^2}{b_i^2}\right) e_i - \frac{\rho}{b_i}[(v_{i+1} - v_i) \times e_i]. \quad (9)$$

In the case that two different indices i and j correspond to the same intersecting sphere $B_i$, then this formula provides the additive contributions from arcs $a_i$ and $a_j$. The generalization to the case when the boundary of the covered area consists of several contours $C_1$, $C_m$ is straightforward.

If an intersecting sphere $B_i$ gives rise to k arcs $a_1, \ldots, a_k$ possibly belonging to different contours $C_1$, $C_m$, the total derivative is the sum of k terms, each of which is given by eq. (9).

Furthermore, the contribution from one contour $C_m$ to the derivative $$\frac{dS}{dr}$$

(with respect to the position of the selected atom) is given by $$\frac{dS}{dr} = -\sum_{i=1}^{n} \frac{dS}{dr_i}. \quad (10)$$

In order to provide an elementary derivation for the accessible area S, it is assumed that the boundary consists of a single contour $C_m$ as illustrated in the drawings. The covered surface can be represented as the union of a central polygon with the vertices $v_1, v_2, \ldots, v_n$ and the caps truncated by the sides of this polygon. The polygon area $S^{(polygon)}$ is $$S^{(polygon)} = \left[\sum_{i=1}^{n} \alpha_i - \pi(n-2)\right] \cdot \rho^2 \quad (11)$$

The area of the i-th truncated cap can be found as the area of the sector with the central angle $\phi_i$ (cf. eq. (1))

$$S_i^{(sector)} \leq (\phi_i/2\pi) S_i^{(cap)} = \phi_i(1-\cos\theta_i) \cdot \rho^2 \quad (12)$$

plus (if $\phi_i > \pi$) or minus (if $\phi_i < \pi$) the area of the triangle with the vertices $v_i$, $v_i+1$ and the center of the i-th cap. For example, the area of the first triangle with $\phi_1 > \pi$ (FIG. 5) is $$S_1^{(triangle)} = [(2\pi - \phi_1) + 2(\beta_1 - \pi/2) - \pi] \cdot \rho^2 = (2\beta_1 - \phi_1) \cdot \rho^2 \quad (13)$$

The area of the second triangle with $\phi_2 < \pi$ is $$S_2^{(triangle)} = [\phi_2 + 2(\pi/2 - \beta_2) - \pi] \cdot \rho^2 = (\phi_2 - 2\beta_2) \cdot \rho^2. \quad (14)$$

In both cases, the area of a truncated cap is given by $$S_i^{(tr.cap)} = (2\beta_i - \phi_i \cos\theta_i) \cdot \rho^2. \quad (15)$$

Using eqs. (11) and (15), the formula for the accessible surface area is:

$$S = \left[2\pi + \sum_{i=1}^{n}(\varphi_i \cos\theta_i + \psi_i - \pi)\right] \cdot \rho^2. \quad (16)$$

A generalization for considering an arbitrary number of contours $C_1$, $C_m$ can be achieved by summing up the contributions from the single contours $C_1$, $C_m$ (given by eq. (16)) and then putting the resulting value to the interval $(0, 4\pi)$ by subtracting $4\pi$ the necessary number of times.

The angle $(\pi - \psi_i)$ can be found as the angle between vectors $[e_{i-1} \times (v_i - r)]$ and $[e_i \times (v_i - r)]$:

$$\cos(\pi - \psi_i) = \frac{e_{i-1} e_i - \cos\theta_{i-1}\cos\theta_i}{\sin\theta_{i-1}\sin\theta_i} \quad (17)$$

(if i=1, then i−1 should be substituted by n). The angle $\phi_i$ can be found as the angle between the vectors $[v_i - (r + e_i \rho \cos\theta_i)]$ and $[v_{i+1} - (r + e_i \rho \cos\theta_i)]$:

$$\cos\varphi_i = \frac{(v_i - r)(v_{i+1} - r) - \rho^2 \cos^2\theta_i}{\rho^2 \sin^2\theta_i} \quad (18a)$$

$$\sin\varphi_i = \frac{e_i[(v_i - r) \times (v_{i+1} - r)]}{\rho^2 \sin^2\theta_i} \quad (18b)$$

Constructing the contour $C_m$ of arcs $a_i$ and identifying the vertices $v_i$ among all the other triple intersections of the atomic spheres, i.e. the intersecting spheres $B_i$, can be achieved by means of a modified Voronoi diagram for the set of spheres $B_i$. The modification is performed in order to take into account that the spheres $B_i$ have different radii $\rho_i$. The vertices $v_i$ are the intersections of the central sphere (i.e. sphere B) with the edges of the corresponding Voronoi cell.

Figure 4:
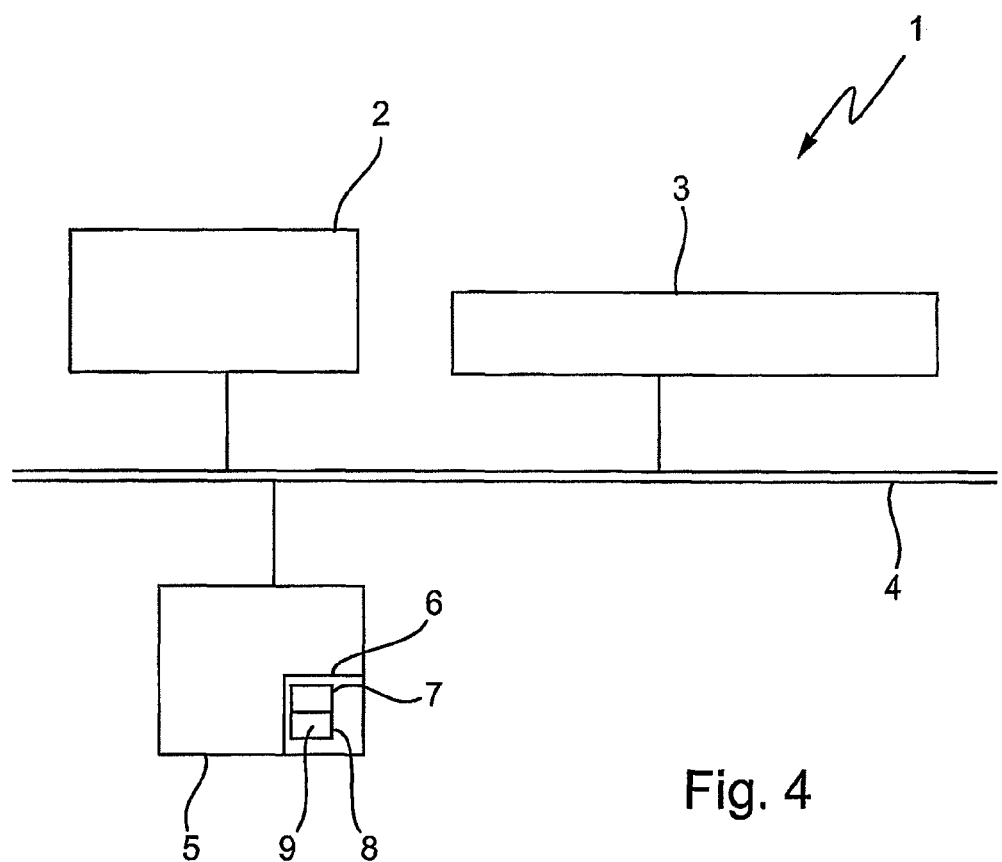
FIG. 4 shows an illustration of a system adapted for executing the inventive method.

FIG. 4 schematically shows an example of a system 1 that is adapted for executing the inventive method.

System 1 comprises a main processor 2 that is connected with a memory element 3 via a bus-system 4, as is commonly known in the art. Memory element 3 can be any known memory, in particular a main memory, and bus-system 4 can be any known bus-system or any other device that enables communication of different system components.

System 1 further comprises at least one special processor 5, e.g. a cell processor, a graphics processing unit (GPU), or a FPGA processor. Special processor 5 further comprises a memory element 6, having a first memory area 7 for storing data and a second memory area 8 for storing instructions. In the second memory area 8, a computer program 9 is stored that comprises an implementation of the inventive method. Thus, computer program 9 comprises instructions that enable system 1 to execute the inventive method, if the instructions of computer program 9 are run on system 1, in particular on special processor 5.

However, the inventive method is not limited to be executed on a system similar to system 1. Even if the inventive method is executed on a system that e.g. only comprises a main memory 2, a significant reduction of the computing time will be achieved due to the reduced number of instructions and intermediate results of the inventive method, which in turn lead to a reduced number of inter-processor communications and/or processor-memory communications.

According to embodiments of the invention, a computer system may include one or more components that may include a bus, a processor, a memory, a read only memory (ROM), a data store, an input device, an output device, and a communication interface. Bus may include one or more interconnects that permit communication among the components of computer system, such as processor, memory, ROM, data store, input device, output device, and communication interface.

The processor or host processor may include any type of processor, microprocessor, or processing logic that may interpret and execute instructions (e.g., a field programmable gate array (FPGA)). The processor may comprise a single device (e.g., a single core) and/or a group of devices (e.g., multi-core). The processor may include logic configured to execute computer-executable instructions configured to implement one or more embodiments. The instructions may reside in the data store, memory, or ROM, and may include associated instructions.

Memory may be a computer-readable medium that may be configured to store instructions configured to implement one or more embodiments. The memory may be a primary storage accessible to the processor and may comprise a random-access memory (RAM) that may include RAM devices, such as Dynamic RAM (DRAM) devices, flash memory devices, Static RAM (SRAM) devices, etc.

ROM may include a non-volatile storage that may store information and computer-executable instructions for processor. The computer-executable instructions may include instructions executed by processor. The data store may be configured to store information and instructions for the processor. Examples of a data store may include a magnetic disk, optical disk, flash drive, floppy discs, CD's etc.

The information and computer-executable instructions and information may be stored on a medium contained in the storage device. Examples of media may include a magnetic disk, optical disk, flash memory, etc. The data store may include a single storage device or multiple storage devices. Moreover, the data store may attach directly to computer system and/or may be remote with respect to computer system and connected thereto via a network and/or another type of connection, such as a dedicated link or channel.

An input device may include any mechanism or combination of mechanisms that may permit information to be input into computer system from, e.g., a user. Input device may include logic configured to receive information for computer system from, e.g. a user. Examples of input device may include a keyboard, mouse, touch sensitive display device, microphone, pen-based pointing device, and/or biometric input device, etc.

Output device may include any mechanism or combination of mechanisms that may output information from the computer system. Output device may include logic configured to output information from computer system. Embodiments of output devices may include displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc.

Communication interface may include logic configured to interface computer system with network and enable computer system to exchange information with other entities connected to network, such as, for example, service provider, target environment and cluster. Communication interface may include any transceiver-like mechanism that enables computer system to communicate with other devices and/or systems, such as a client, a server, a license manager, a vendor, etc. The communications may occur over a communication medium, such as a data network. Communication interface may include one or more interfaces that are connected to the communication medium. The communication medium may be wired or wireless. Communication interface may be implemented as a built-in network adapter, network interface card (NIC), Personal Computer Memory Card International Association (PCMCIA) network card, card bus network adapter, wireless network adapter, Universal Serial Bus (USB) network adapter, modem or any other device suitable for interfacing computer system to any type of network.

It will be understood that the above description of the present invention and attachments are susceptible to various modifications, changes and adaptations, and the same are intended to be comprehended within the meaning and range of equivalents of the appended claims.

The invention claimed is:

1. A method for performing a molecular dynamics simulation for determining the solvent accessible surface area of a molecule (M) with respect to atomic coordinates, the molecule (M) comprising a plurality of atoms, a sphere ($B_i$) being assigned to each atom, and each sphere ($B_i$) comprising a radius ($\rho_i$) and a center position ($r_i$) the method comprising:
   determining, by a computer, for each sphere (B) all neighbouring spheres ($B_i$) that intersect with the sphere (B);
   defining, by the computer, a set of one or more contours ($C_m$), such that all intersecting circles of sphere B with spheres $B_i$ intersect on the surface of sphere B;
   determining, by the computer, for each contour ($C_m$) an area enclosed by the contour ($C_m$), wherein the contour ($C_m$) comprises the area on the surface of said sphere (B) that is enclosed by one or more arcs ($a_1$, $a_2$, $a_3$) resulting from an intersection of the surface of said sphere (B) with one of the surface of one intersecting sphere ($B_i$) or the surfaces of a plurality of intersecting spheres ($B_i$) that have an overlapping intersection area on the surface of said sphere (B);
   determining, by the computer, the solvent accessible surface (S) of said sphere (B) as the surface of said sphere (B) subtracted by the area comprised by all contours ($C_m$) on the surface of said sphere (B);
   determining, by the computer, the solvent accessible surface area of the molecule (M) based on a sum of solvent accessible surface areas ($S_i$) of the spheres; and
   determining, by the computer, the derivative $$\left(\frac{dS}{dr_i}\right)$$

of the solvent accessible surface area (S) of said sphere (B) with respect to the position ($r_i$) of the intersecting spheres ($B_i$) satisfying the formula:

$$\frac{dS}{dr_i} = \frac{\varphi_i \rho}{2}\left(1 + \frac{\rho^2 - \rho_i^2}{b_i^2}\right)e_i - \frac{\rho}{b_i}[(v_{i+1} - v_i) \times e_i],$$

wherein
S is the solvent accessible surface area of said sphere (B);
$r_i$ is the center of an intersecting sphere ($B_i$);
$\rho$ is the radius of said sphere (B);
$\rho_i$ is the radius of the intersecting sphere ($B_i$);
$b_i = |r - r_i|$ is the distance between the center (r) of said sphere (B) and the center ($r_i$) of the intersecting ($B_i$);
$e_i = (r_i - r)/b_i$ is the unit vector from the center (r) of said sphere (B) to the center ($r_i$) of the intersecting sphere $B_i$; and
$v_i$ is the endpoint of an arc ($a_i$), wherein arc ($a_i$) is the part of the intersection line ($I_i$) that contributes to the contour ($C_m$).

2. The method according to claim 1, further comprising:
   determining, by the computer, a force acting on an atom based on the derivative $\left(\dfrac{dS}{dr_i}\right)$ of the solvent accessible surface area (S) with respect to the position (r, $r_i$) of the spheres (B, $B_i$).

3. The method according 1, further comprising:
   determining, by the computer, the solvent accessible surface area of the atom (S) using the following formula:

$$S = \left[2\pi + \sum_{i=1}^{n}(\varphi_i \cos\theta_i + \psi_i - \pi)\right] \cdot \rho^2$$

with $$\cos\theta_i = \frac{1}{2\rho}\left(b_i + \frac{\rho^2 - \rho_i^2}{b_i}\right),$$

wherein
   $\psi_i$ is the exterior angle of the i-th arc ($a_i$);
   $\phi_i$ is the central angle of the i-th arc ($a_i$); and
   $\theta_i$ is the angular radius of a cap ($cap_i$) of sphere ($B_i$) that overlaps with said sphere (B).

4. The method according to claim 1, further comprising:
   determining, by the computer, endpoints ($v_i$) of arc ($a_i$) of each sphere ($B_i$) based on a modified Voronoi diagram, wherein the Voronoi diagram is modified for taking different radii of different intersecting spheres ($B_i$) into account.

5. A computer-implemented system for determining the derivatives of the solvent accessible surface area of a molecule (M), the molecule (M) comprising a plurality of atoms, a sphere (B, $B_i$) being assigned to each atom, the sphere (B, $B_i$) comprising a radius ($\rho$, $\rho_i$) and a center position (r, $r_i$), the system comprising:
   a processor configured to:
      determine for each sphere (B) all neighbouring spheres ($B_i$) that intersect with the sphere (B);
      define a set of one or more contours ($C_m$), such that all intersecting circles of sphere B with spheres $B_i$ intersect on the surface of sphere B;
      determine for each contour ($C_m$) an area enclosed by the contour ($C_m$), wherein the contour ($C_m$) includes the area on the surface of said sphere (B) that is enclosed by one or more arcs ($a_1$, $a_2$, $a_3$) resulting from an intersection of the surface of said sphere (B) with one of the surface of one intersecting sphere ($B_i$) or the surfaces of a plurality of intersecting spheres ($B_i$) that have an overlapping intersection area on the surface of said sphere (B);
      determine the solvent accessible surface (S) of said sphere (B) as the surface of said sphere (B) subtracted by the area comprised by all contours ($C_m$) on the surface of said sphere (B);
      determine, using the processor, the solvent accessible surface area of the molecule (M) based on a sum of solvent accessible surface areas ($S_i$) of the spheres; and
      determine derivatives of the solvent accessible surface area of the molecule (M) depending on a sum of a derivatives of the solvent accessible surface areas of its atoms, wherein the derivatives $\left(\dfrac{dS}{dr_i}\right)$ of the solvent accessible surface area (S) of said sphere (B) with respect to the position ($r_i$) of the intersecting spheres ($B_i$) satisfy the formula:

$$\frac{dS}{dr_i} = \frac{\varphi_i \rho}{2}\left(1 + \frac{\rho^2 - \rho_i^2}{b_i^2}\right)e_i - \frac{\rho}{b_i}[(v_{i+1} - v_i) \times e_i],$$

wherein
   S is the solvent accessible surface area of said sphere (B);
   $r_i$ is the center of an intersecting sphere ($B_i$);
   $\rho$ is the radius of said sphere (B);
   $\rho_i$ is the radius of the intersecting sphere ($B_i$);
   $b_i = |r - r_i|$ is the distance between the center (r) of said sphere (B) and the center ($r_i$) of the intersecting sphere ($B_i$);
   $e_i = (r_i - r)/b_i$ is the unit vector from the center (r) of said sphere (B) to the center ($r_i$) of the intersecting sphere $B_i$; and
   $v_i$ is the endpoint of an arc ($a_i$), wherein arc ($a_i$) is the part of the intersection line ($I_i$) that contributes to the contour ($C_m$).

6. A processor in a system for performing a molecular dynamics simulation, wherein the processor is programmed with a computer program to perform the method according to claim 1.

7. A computer-readable storage medium, the storage medium encoded with computer-readable program code that when executed cause a computer to perform a molecular dynamics simulation for determining the solvent accessible surface area of a molecule (M) with respect to atomic coordinates, the molecule (M) comprising a plurality of atoms, a sphere ($B_i$) being assigned to each atom, and each sphere ($B_i$) comprising a radius ($\rho_i$) and a center position ($r_i$), the program code comprising instructions for:
   determining for each sphere (B) all neighbouring spheres ($B_i$) that intersect with the sphere (B);
   defining a set of one or more contours ($C_m$), such that all intersecting circles of sphere B with spheres $B_i$ intersect on the surface of sphere B;
   determining for each contour ($C_m$) an area enclosed by the contour ($C_m$), wherein the contour ($C_m$) includes the area on the surface of said sphere (B) that is enclosed by one or more arcs ($a_1$, $a_2$, $a_3$) resulting from an intersection of the surface of said sphere (B) with one of the surface of one intersecting sphere ($B_i$) or the surfaces of a plurality of intersecting spheres ($B_i$) that have an overlapping intersection area on the surface of said sphere (B);
   determining the solvent accessible surface (S) of said sphere (B) as the surface of said sphere (B) subtracted by the area comprised by all contours ($C_m$) on the surface of said sphere (B);
   determining the solvent accessible surface area of the molecule (M) based on a sum of solvent accessible surface areas ($S_i$) of the spheres; and
   determining, by the computer, the derivative $$\left(\frac{dS}{dr_i}\right)$$

of the solvent accessible surface area (S) of said sphere (B) with respect to the position ($r_i$) of the intersecting spheres ($B_i$) satisfy the formula:

$$\frac{dS}{dr_i} = \frac{\varphi_i \rho}{2}\left(1 + \frac{\rho^2 - \rho_i^2}{b_i^2}\right)e_i - \frac{\rho}{b_i}[(v_{i+1} - v_i) \times e_i],$$

wherein
S is the solvent accessible surface area of said sphere (B);
$r_i$ is the center of an intersecting sphere ($B_i$);
$\rho$ is the radius of said sphere (B);
$p_i$ is the radius of the intersecting sphere ($B_i$);
$b_i = |r - r_i|$ is the distance between the center (r) of said sphere (B) and the center ($r_i$) of the intersecting sphere ($B_i$);
$e_i = (r_i - r)/b_i$ is the unit vector from the center (r) of said sphere (B) to the center ($r_i$) of the intersecting sphere $B_i$; and
$v_i$ is the endpoint of an arc ($a_i$), wherein arc ($a_i$) is the part of the intersection line ($I_i$) that contributes to the contour ($C_m$).

8. The storage medium according to claim 7, wherein the storage medium comprises a magnetic or an optical medium.

9. The storage medium according to claim 7, wherein the program code further comprises instructions for:
determining derivatives of the solvent accessible surface area of the molecule (M) depending on a sum of the derivatives of the solvent accessible surface areas of its atoms.

* * * * *